(12) United States Patent
Gaudyn

(10) Patent No.: US 9,968,205 B1
(45) Date of Patent: May 15, 2018

(54) INFANT SLEEPING BAG, BLANKET AND SHEET

(71) Applicant: Halina Gaudyn, Park Ridge, IL (US)

(72) Inventor: Halina Gaudyn, Park Ridge, IL (US)

(*) Notice: Subject to any disclaimer, the term of this patent is extended or adjusted under 35 U.S.C. 154(b) by 0 days. days.

(21) Appl. No.: 15/655,473

(22) Filed: Jul. 20, 2017

(51) Int. Cl.
| A47D 15/00 | (2006.01) |
| A47D 13/06 | (2006.01) |
| A47G 9/02 | (2006.01) |
| A47D 9/00 | (2006.01) |
| A47G 9/04 | (2006.01) |
| A61M 21/02 | (2006.01) |

(52) U.S. Cl.
CPC ......... *A47D 15/008* (2013.01); *A47D 9/00* (2013.01); *A47D 13/06* (2013.01); *A47G 9/0223* (2013.01); *A47G 9/0246* (2013.01); *A47G 9/04* (2013.01); *A61M 21/02* (2013.01)

(58) Field of Classification Search
CPC ... A47D 5/00; A47D 7/00; A47D 9/00; A47D 13/06; A47D 13/063; A47D 13/08; A47D 15/00; A47D 15/001; A47D 15/005; A47D 15/008; A47G 9/0238; A47G 9/0246
USPC ... 5/93.1, 655, 652, 485, 482, 494, 497, 499
See application file for complete search history.

(56) References Cited

U.S. PATENT DOCUMENTS

| 4,989,286 A * | 2/1991 | Tucker | A47D 15/008 128/872 |
| 5,189,744 A * | 3/1993 | Roberts | A47G 9/0246 5/497 |
| 6,502,258 B1 * | 1/2003 | Mitchell | A47G 9/0246 5/497 |
| 7,441,288 B2 * | 10/2008 | Johnson | A47C 21/024 5/485 |
| 8,127,385 B1 * | 3/2012 | Goutevenier | A47D 13/08 5/633 |
| 8,302,230 B1 * | 11/2012 | Jarrett, Jr. | A47D 13/083 128/875 |
| 8,572,782 B1 * | 11/2013 | Amini | A47D 15/008 5/485 |
| 2007/0240262 A1 * | 10/2007 | Johnson | A47C 21/024 5/485 |

* cited by examiner

*Primary Examiner* — Robert G Santos
(74) *Attorney, Agent, or Firm* — Charles F. Meroni, Jr.; Meroni & Meroni, PC

(57) ABSTRACT

An apparatus for improved sleep made up of a mattress, and a sleep aid, on a first end of the mattress the sleep aid being a partially fitted sheet, the fitted sheet tucked into and secured onto a side of the mattress, and on a second end of the mattress the sleep aid being a blanket, the blanket attached to the fitted sheet and the blanket being large enough to be folded over an infant, the fitted sheet having hook and loop fasteners and the blanket having matable hook and loop fasteners situated on the blanket opposite the fitted sheet, such that when the blanket is folded over and the hook and loop fasteners are mated a pocket capable of containing an infant is formed.

17 Claims, 3 Drawing Sheets

INFANT SLEEPING BAG, BLANKET AND SHEET

RELATED APPLICATIONS

This application claims the benefit of application Ser. No. 15/530,383 filed 5 Jan. 2017 and application Ser. No. 15/731,292 filed 17 May 2017.

FIELD OF THE INVENTION

The present disclosure generally relates to blankets, sheets, pillows, sleeping backs and other related devices, more particularly to a sheet and blanket combination for securing an infant during sleep.

BACKGROUND

There are a variety of infant blankets and coverings for infants present in the art. In the past many designs functioned only to keep an infant warm while sleeping. Today significantly more is known about infant sleeping patterns and sleeping safety. The concern for infant warmth is now shared with the concern for infant comfort and safety. Some infants frequently change positions while sleeping, so it is desirable to make an infant's sleeping environment as free as possible of suffocation hazards while at the same time insuring the infant is kept in a secure sleeping position.

For example, according to the most recent recommendations of the American Academy of Pediatrics (AAP), an infant should be placed on his or her back on a firm sleeping surface with a tight-fitting sheet and the surface without soft bedding for at least the first year of the child's life. The newest AAP guidelines also condone swaddling the infant, provided the blanket is secure and the infant is able to move his or her hips. These recommendations are intended to reduce the risk of Sudden infant Death Syndrome (SIDS), which doctors at the AAP believe may be linked to the strangulation or choking of the infant on soft bedding or sheets within a crib or other sleeping surface.

Previous devices have attempted to solve this problem with varying degrees of success, however none have fully addressed the issues. Examples follow.

U.S. Pat. No. 2,677,834 by Moynihan discloses a blanket secured to the side of a crib with snap fasteners and a single additional strap for securing the infant to the blanket.

U.S. Pat. No. 3,845,513 by Hubner discloses a zipper opening blanket of resilient material having a bodice-like upper portion and a bag-like lower portion is secured to a crib mattress by a back portion sewn jointly with a soft absorbant filler and a retainer for a disposable diaper to a stretchable bedlinen sheet and a tension band surrounding the mattress.

U.S. Pat. No. 4,202,052 by Bilanzich discloses a crib sheet for retaining an infant in a central region of a crib or bed and preventing such an infant from displacing a blanket covering when unattended. The sheet includes a central pleat which extends along the entire sheet length and is sewed or otherwise fixed in a folded configuration at the ends thereof. A sleeper jacket is attached at an opening across the central pleat to form an integral sleeper unit. The extendable pleat between the fixed ends permits safe movement for the infant without binding the sheet or causing other discomfort.

U.S. Pat. No. 5,241,300 by Buschmann discloses a transilluminated optical fiber is placed adjacent to an infant's respiratory moving parts using an elastic fabric. Use is made of the effect that moving the fiber causes a modulation of the intensity of the transmitted light to monitor the infant's breathing pattern to avoid S(udden) I(nfant) D(eath) S(yndrome).

U.S. Pat. No. 6,301,729 by Hall discloses a crib safety sack made of thin blanket fabric is provided. The sack is pocket-shaped to cover an end of a crib mattress. The top panel of the sack secures an infant in a back sleeping position on the surface of the crib mattress, which is the sleeping position recommended by experts for the prevention of SIDS. The sack acts as a blanket and also as a safety restraint keeping the infant securely in position through gentle force. The sack may be reversible, in that either a top or bottom panel of the sack may be positioned on top of the mattress. The sack preferably has at least one flap providing easy access.

U.S. Pat. No. 6,450,168 by Nguyen discloses an infant's sleep blanket/garment for use with medical monitoring devices, which is offered as either a sleep sack or a sleep shirt, depending on the age of the infant, with the sleep sack further presented with no arm holes and having snugging straps for newborns or with arm holes and sleeves for older infants. An openable monitor cable sheath located inside of the sleeper allows for bundling medical monitoring device cables and IV tubes and enclosing them within the sheath to prevent irritation to the infant and reduce the possibility of the infant becoming entangled in the cables and tubes. Additionally, the upper shoulder and sleeve seams are openable to allow for the installation, maintenance and removal of IV tubes without removing the garment from the infant. Thermometers incorporated into the body of the garment and an optional sleep cap aid in monitoring the infant's temperature as he sleeps.

U.S. Pat. No. 8,020,226 by Landry discloses a crib safety sheet and separable blanket with a sheet portion for selectively removing at least the blanket from the sheet, when the sheet is attached to a sleep surface. The separable blanket defining at least two edges for wrapping the blanket about an infant. The blanket may be removed from the sheet by separating the blanket, or by separating a sheet material portion attached to the blanket, from the sheet covering the sleep surface.

While AAP guidelines suggest sparse sleeping arrangements for infants, parents still want to ensure that their children are in a warm, comfortable environment during sleep. As such, there are competing desires between preventing strangulation, SIDS, and other issues, and with providing a comfortable sleeping environment for the child (improving quality of life for both the child and the parents).

These problems, and others, are addressed by the present invention and discussed in greater detail below.

BRIEF SUMMARY

Currently-available devices lack many of the proposed features described below. The infant sleeping bag of the present disclosure allows parents to provide children with a warm blanket that does not pose a strangulation threat that will stay in place even as a child moves during the night (unlike a swaddling blanket), thereby reducing the risk of strangulation and SIDS.

The infant sleeping bag, blanket & sheet of the present disclosure is therefore a fitted sheet combined with a blanket. One end of the device consists of a fitted sheet with an elastic pocket and a firm, slanted mattress pad to provide a slight elevation for the infant's head. The elevation declines towards the feet of the infant. The fitted sheet may also have hook and loop (Velcro) fasteners to connect it to the blanket.

The other end, is a blanket portion that is intended to extend across the remaining length of a crib mattress while folded over. Thus, the infant is both resting on and covered by the blanket portion of the device when in use. The blanket also is fitted with hook and loop fasteners to connect it to the fitted sheet. This ensures the blanket will stay in place when the infant sleeps, without significantly restricting the infant's movement.

The advantages of such an application become clear when one is experienced in caring for infants, cribmaking, quilting, upholstery, and related fields. Typical devices currently on the market do not have the confluence and plethora of features contemplated and described herein.

In a first embodiment the disclosure contemplates an apparatus for improved sleep including mattress; and a sleep aid, on a first end of the mattress the sleep aid being a partially fitted sheet, the fitted sheet tucked into and secured onto a side of the mattress, and on a second end the sleep aid being a blanket, the blanket attached to the fitted sheet and the blanket being large enough to be folded over an infant; the fitted sheet having hook and loop fasteners and the blanket having matable hook and loop fasteners situated on the blanket opposite the fitted sheet, such that when the blanket is folded over and the hook and loop fasteners are mated a pocket capable of containing an infant is formed.

In a second embodiment the disclosure contemplates an apparatus for improving the sleep of infants including a partially fitted sheet, the fitted sheet capable of being tucked into and secured onto a side of a mattress; a blanket, the blanket attached to the fitted sheet and the blanket being large enough to be folded over an infant; the fitted sheet having hook and loop fasteners and the blanket having matable hook and loop fasteners situated on the blanket opposite the fitted sheet, such that when the blanket is folded over and the hook and loop fasteners are mated a pocket capable of containing an infant is formed.

In another embodiment the disclosure contemplates a method for safely covering an infant including at least the steps of providing a mattress; and a sleep aid, on a first end of the mattress the sleep aid being a partially fitted sheet, the fitted sheet tucked into and secured onto a side of the mattress, and on a second end of the mattress the sleep aid being a blanket, the blanket attached to the fitted sheet and the blanket being large enough to be folded over the infant; the fitted sheet having hook and loop fasteners and the blanket having matable hook and loop fasteners situated on the blanket opposite the fitted sheet, such that when the blanket is folded over and the hook and loop fasteners are mated a pocket capable of containing an infant is formed; placing the infant on top of the fitted sheet and a portion of the blanket; folding over the blanket; and securing the hook and loose fasteners on the blanket to the hook and loop fasteners on the fitted sheet, thereby covering the infant.

Such embodiments do not represent the full scope of the invention. Reference is made therefore to the claims herein for interpreting the full scope of the invention. Other objects of the present invention, as well as particular features, elements, and advantages thereof, will be elucidated or become apparent from, the following description and the accompanying drawing figures.

DESCRIPTION OF THE DRAWINGS

The present invention may be better understood, and its numerous objects, features, and advantages made apparent to those skilled in the art by referencing the accompanying drawings.

DETAILED DESCRIPTION

Referring now the drawings with more specificity, the present invention essentially provides an improved infant sleeping bag, fitted sheet, and blanket assembly and apparatus. The preferred embodiments of the present invention will now be described with reference to FIGS. 1-6 of the drawings. Variations and embodiments contained herein will become apparent in light of the following descriptions.

Figure 1:
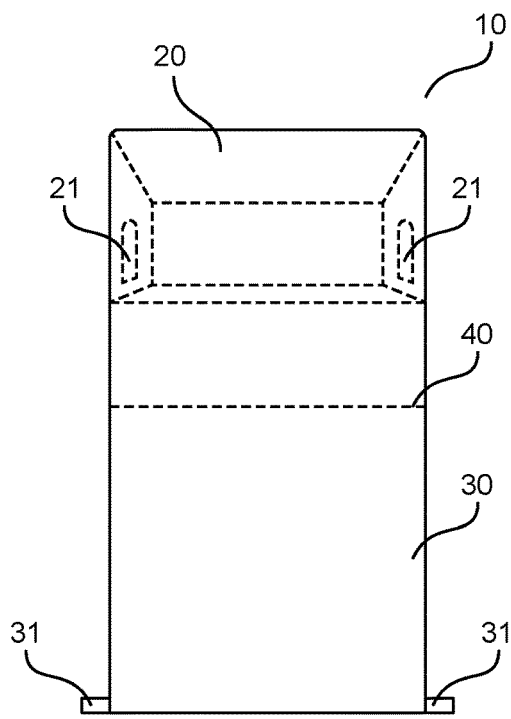
FIG. 1 is a top down view of an infant sleeping bag, blanket, and sheet according to the present disclosure.
Figure 2:
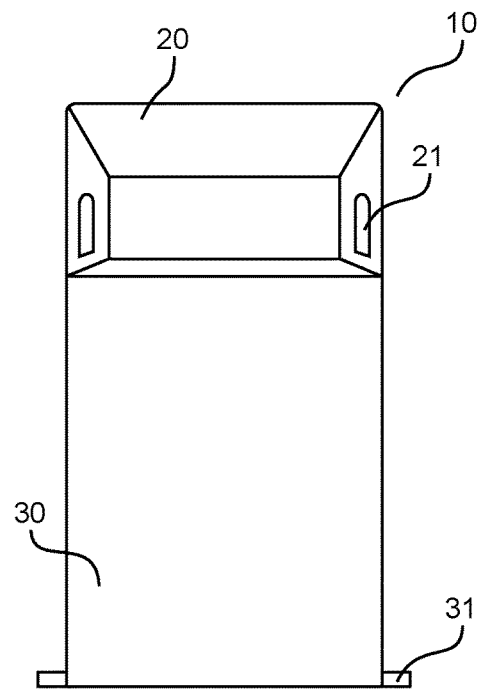
FIG. 2 is a bottom up view of the infant sleeping bag, blanket, and sheet according to the present disclosure.

Looking now to FIGS. 1 & 2 a sleeping bag 10, is shown. As described herein, bag 10 is made up of at least a partially fitted sheet 20 and a blanket 30. The sheet 20 and blanket 30 can be contiguous and fold at folding line 40 or may be made from separate materials. As shown the sheet can be fitted with hook and loop fasteners 21 that are matable with hook and loop fasteners 31 on the blanket portion of the sleeping apparatus 10.

Figure 3:
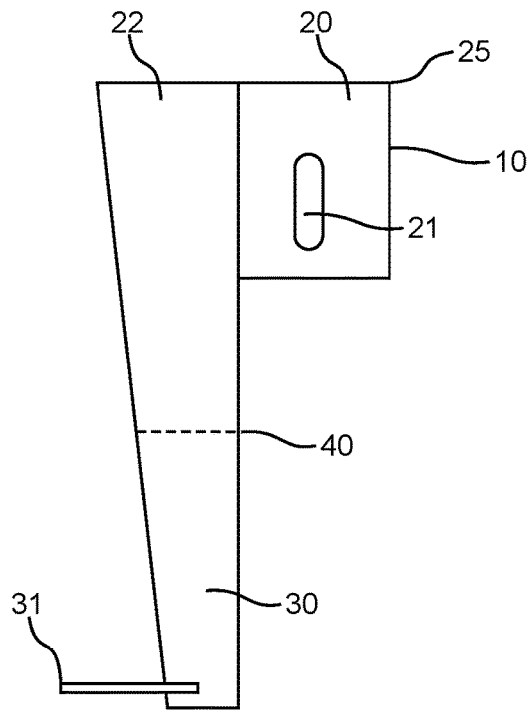
FIG. 3 is a right side view of the infant sleeping bag, blanket, and sheet according to the present disclosure.
Figure 4:
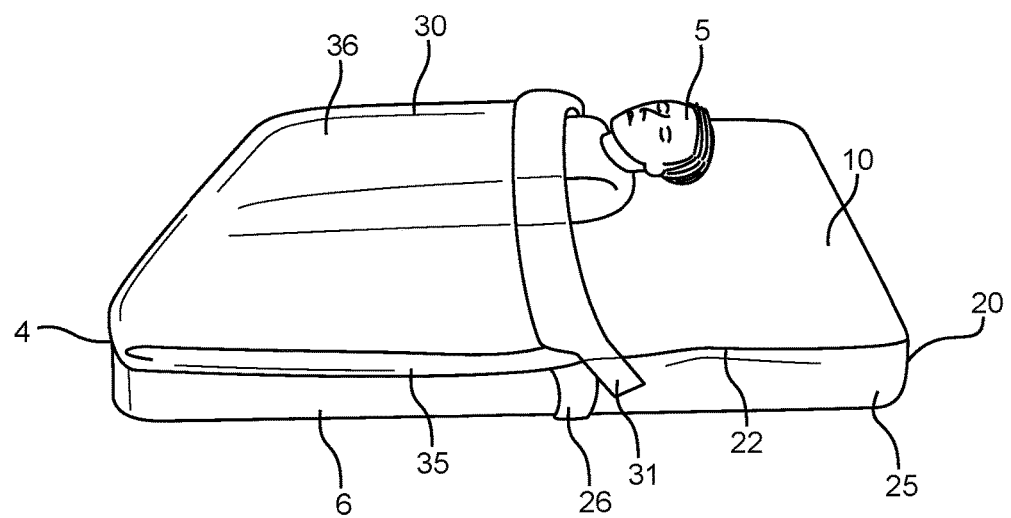
FIG. 4 a side angled view of the infant sleeping bag, blanket, and sheet in use by a child according to the present disclosure.

As can be seen in greater detail in FIGS. 3 & 4 the combination 10 of fitted sheet 20 and blanket 30 can secure an infant 5 in place on a crib mattress 6. As is evident in FIG. 3, the combination has a slight incline 22 from head to toe in a normal configuration. This small incline 22 is provided by a small, tapered, mattress pad attached to the underside of the fitted sheet 20. Such an incline 22 can help infants 5 sleep, particularly those suffering from gastro-esophageal reflux or upset stomachs. However, a baby need not have issues for this incline 22 to provide advantages, as it aids in the release of burps and normal gas. Typically this incline is no more than 1.25 inches, however, for larger babies a thickness of up to three inches can be used. The incline is made of a fairly firm material and tapers down to just a sheet at the transition line 23. The end 25 of the fitted sheet 20 should be tucked under one side of the mattress for proper securing of the apparatus 10. In addition, some embodiments may incorporate an elastic band 26 that allows for the apparatus 10 to fit tautly onto the mattress 6.

In addition to the fitted sheet 20, the apparatus 10 incorporates a blanket 30. The blanket 30 spans the length of a crib mattress when unfolded. When an infant 5 is put to sleep, the blanket 30 can be folded over 40 and secured using straps 31 that have hook and loop fasteners which are matable with the hook and loop fasteners 21 on the fitted sheet 20. As can be seen in FIG. 4, the infant 5 rests on the bottom portion 45 of the blanket 40 which lies flat against the mattress 6, while the top portion of the blanket 36 is folded on top of the infant 6 to keep him or her warm. Because the blanket 30 is merely folded and secured by straps 31, the infant is still capable of small movements, unlike the constriction of a traditional wrap used in swaddling. The blanket 30 is typically around 25-30 inches in length, or whatever length keeps the baby's head from sliding off the slanted mattress 22. This allows for better sleeping in many infants and also decreases the risk of strangulation and SIDS associated with loose blankets.

Figure 5:
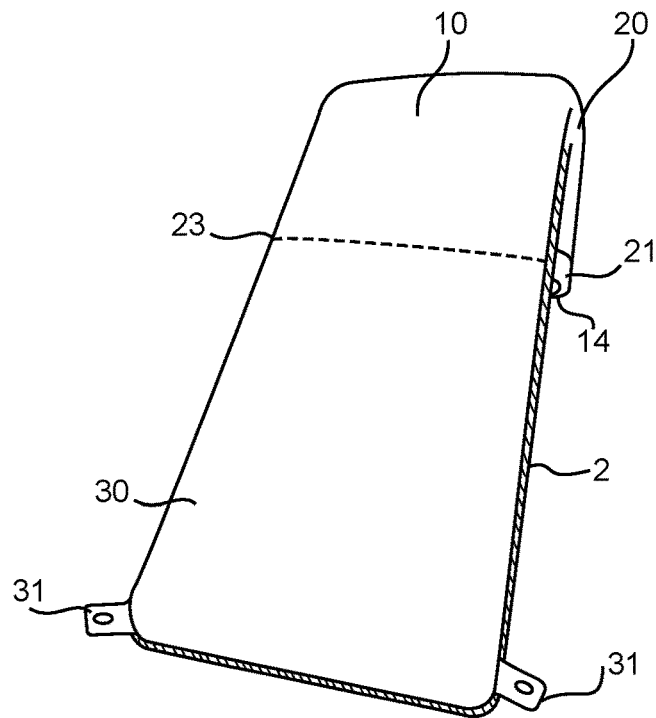
FIG. 5 is a front side isometric view of the infant sleeping bag, blanket, and sheet in an unfolded state according to the present disclosure.
Figure 6:
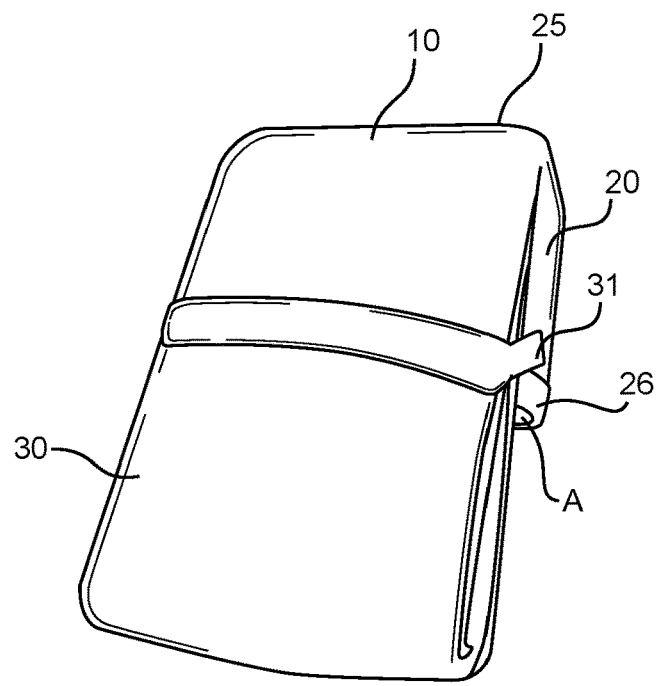
FIG. 6 is a front side isometric view of the infant sleeping bag, blanket, and sheet in a folded state according to the present disclosure.

Looking now to FIG. 5, the apparatus 10 is shown in its unfolded and unused state. As can be clearly seen, hook and loop fasteners 31 can be attached to straps on blanket 30, as can be seen, the hook and loop fasteners 21 on fitted sheet 20 are positioned such that when blanket 30 is folded (depicted in FIG. 6) they align with fasteners 31. Conversely, as seen in FIG. 6, the blanket 30 is folded over such that the hook and loop fasteners 21, 31 are aligned on both the sheet 20 and blanket 30 portions of the device 10. One can see a small portion of the open end of the fitted sheet 20 at point 'A' which would normally tucked under a mattress 6.

Although all of the possible angles and types of deployments are not shown, other methods of attaching the sleeping bad 10 to a crib or mattress 6 according to this disclosure should be readily apparent to those skilled in the art.

INDUSTRIAL APPLICABILITY

A combination fitted sheet 20 and blanket 30 apparatus composed of a soft cotton material can aid in infant sleep and SIDS prevention. To secure the apparatus 10 in place an elastic band 26 can be utilized to further secure the fitted sheet 20 to a bed or crib. The fitted sheet 20, may also have an inclined mattress pad 22 for supporting the head of an infant in an elevated position, however the taper on such a pad must be such that it does not interfere with folding of the blanket 30, as hook and loop fasteners 31 on the blanket are attached to hook and loop fasteners 21 on the fitted sheet when the apparatus 10 is deployed.

As may be clear to those skilled in the art, the elastic band 26 in the fitted sheet 20 is sized to fit around a crib mattress. Because the sheet 20 and bedding 22 will lie flat against the mattress 6, there will not be excess, loose, fabric that poses a risk to a sleeping infant 5. Similarly the hook and loop fasteners 21, 31, ensure the child does not move excessively and also reduces the amount of fabric in the blanket portion 30 that poses a strangulation risk. As such, risk of SIDS is reduced while comfort is maintained.

The parts of the infant sleeping bag or apparatus 10 can be sewn together in various ways to increase wash ability as well as the quality of the product. In many instances, it is desired for the fitted sheet 20, mattress pad 22, and blanket 30 portions to be of varying sizes and thicknesses (to keep the infant comfortable). In such cases a line of sticking divides the two, this also represents folding line 40 in those implementation. For hotter days or climates a single sheet may be preferable.

Accordingly, although the invention has been described by reference to certain preferred and alternative embodiments, it is not intended that the novel arrangements be limited thereby, but that modifications thereof are intended to be included as falling within the broad scope and spirit of the foregoing disclosures and the appended drawings.

I claim:

1. An apparatus for improved sleep comprising:
    a mattress; and
    a sleep aid, on a first end of the mattress the sleep aid being a partially fitted sheet, the fitted sheet tucked into and secured onto a side of the mattress, and on a second end of the mattress the sleep aid being a blanket, the blanket attached to the fitted sheet and the blanket being large enough to be folded over an infant;
    the fitted sheet having hook and loop fasteners and the blanket having matable hook and loop fasteners situated on the blanket opposite the fitted sheet, such that when the blanket is folded over and the hook and loop fasteners are mated a pocket capable of containing an infant is formed, said pocket configured to cover the arms, legs, and torso of the infant;
    the fitted sheet containing a slanted mattress pad and an elastic band, the mattress pad sewn into the bottom of the fitted sheet and tapering towards the blanket, the elastic band, the elastic band running through the fitted sheet and securing the sleep aid to the mattress.

2. The apparatus of claim 1 wherein:
    the blanket and the partially fitted sheet are made out of two different materials.

3. The apparatus of claim 1 wherein:
    the mattress pad is 1.25 inches at its greatest thickness.

4. The apparatus of claim 1 wherein:
    the blanket is configured to secure the infant to the mattress to reduce the risk of strangulation and SIDS.

5. The apparatus of claim 4 wherein:
    the hook and loop fasteners are connected to the blanket by a pair of straps.

6. The apparatus of claim 5 wherein:
    the hook and loop fasteners are connected to the fitted sheet by a pair of straps.

7. The apparatus of claim 6 further comprising:
    a crib, the crib housing the mattress and sleep aid.

8. An apparatus for improving the sleep of infants comprising:
    a partially fitted sheet, the fitted sheet capable of being tucked into and secured onto a side of a mattress;
    a blanket, the blanket attached to the fitted sheet and the blanket being large enough to be folded over an infant;
    the fitted sheet having hook and loop fasteners and the blanket having matable hook and loop fasteners situated on the blanket opposite the fitted sheet, such that when the blanket is folded over and the hook and loop fasteners are mated a pocket capable of containing the infant is formed said pocket configured to cover the arms, legs, and torso of the infant, the hook and loop fasteners being connected to the blanket by a pair of straps and connected to the fitted sheet by a pair of straps.

9. The apparatus of claim 8 wherein:
    the fitted sheet further comprises a slanted mattress pad, the mattress pad sewn into the bottom of the fitted sheet and tapering towards the blanket.

10. The apparatus of claim 9 wherein:
    the mattress pad is 1.25 inches at its greatest thickness.

11. The apparatus of claim 10 wherein:
    the fitted sheet further comprises an elastic band, the elastic band running through the fitted sheet and securing the sleep aid to the mattress.

12. The apparatus of claim 11 wherein:
    the fitted sheet and blanket are composed of two, different, cotton materials.

13. A method for safely covering an infant comprising:
    providing a mattress; and a sleep aid, on a first end of the mattress the sleep aid being partially fitted sheet, the fitted sheet tucked into and secured onto a side of the mattress, and on a second end of the mattress the sleep aid being a blanket, the blanket attached to the fitted sheet and the blanket being large enough to be folded over the infant; the fitted sheet having hook and loop fasteners and the blanket having matable hook and loop fasteners situated on the blanket opposite the fitted sheet, such that when the blanket is folded over and the hook and loop fasteners are mated a pocket capable of containing the infant is formed, said pocket covering the arms, legs, and torso of the infant;

placing the infant on top of the fitted sheet and a portion of the blanket;

folding over the blanket; and securing the hook and loop fasteners on the blanket to the hook and loop fasteners on the fitted sheet, thereby covering the infant.

14. The method of claim 13 wherein:
the fitted sheet further comprises a slanted mattress pad, the mattress pad sewn into the bottom of the fitted sheet and tapering towards the blanket and the infant's head is placed on the thicker end of the mattress pad.

15. The method of claim 14 wherein:
the mattress pad is 1.25 inches at its greatest thickness.

16. The method of claim 13 wherein:
the fitted sheet further comprises an elastic band, the elastic band running through the fitted sheet; and
securing the elastic band around the mattress to secure the sleep aid in place.

17. The method of claim 13 wherein:
the hook and loop fasteners are connected to the blanket by a pair of straps.

\* \* \* \* \*